(12) United States Patent
Carpenter

(10) Patent No.: US 12,156,985 B2
(45) Date of Patent: Dec. 3, 2024

(54) ARRANGEMENT FOR SUPPORTING MEDICAMENT DELIVERY DEVICES AND SYSTEM

(71) Applicant: SHL MEDICAL AG, Zug (CH)

(72) Inventor: Lucas Carpenter, New Taipei (TW)

(73) Assignee: SHL Medical AG, Zug (CH)

( * ) Notice: Subject to any disclaimer, the term of this patent is extended or adjusted under 35 U.S.C. 154(b) by 917 days.

(21) Appl. No.: 16/972,512

(22) PCT Filed: Nov. 20, 2019

(86) PCT No.: PCT/EP2019/081915
§ 371 (c)(1),
(2) Date: Dec. 4, 2020

(87) PCT Pub. No.: WO2020/120086
PCT Pub. Date: Jun. 18, 2020

(65) Prior Publication Data
US 2021/0268171 A1   Sep. 2, 2021

(30) Foreign Application Priority Data

Dec. 13, 2018 (EP) ..................................... 18212151

(51) Int. Cl.
*A61M 5/00* (2006.01)
*A61M 15/00* (2006.01)

(52) U.S. Cl.
CPC ........ *A61M 5/008* (2013.01); *A61M 15/0001* (2014.02)

(58) Field of Classification Search
CPC .................. A61M 5/001; A61M 5/008; A61M 2209/084; B01L 9/06; B65D 23/001; F16M 11/04; A61J 1/16; A47F 1/126

USPC ......................................................... 206/366
See application file for complete search history.

(56) References Cited

U.S. PATENT DOCUMENTS

| | | | |
|---|---|---|---|
| 2,091,126 A | 8/1937 | Speer | |
| 4,024,950 A | 5/1977 | Werth | |
| 5,325,965 A | 7/1994 | Kelley | |
| 6,116,449 A * | 9/2000 | Chiesi | B65D 1/095 |
| | | | 206/820 |

(Continued)

FOREIGN PATENT DOCUMENTS

| | | |
|---|---|---|
| EP | 2420268 A2 | 2/2012 |
| EP | 2574357 A1 | 4/2013 |

(Continued)

OTHER PUBLICATIONS

International Search Report and Written Opinion for Int. App. No. PCT/EP2019/081915, mailed Jan. 16, 2020.

*Primary Examiner* — Anthony D Stashick
*Assistant Examiner* — Raven Collins
(74) *Attorney, Agent, or Firm* — McDonnell Boehnen Hulbert & Berghoff LLP

(57) ABSTRACT

An arrangement for supporting a plurality of medicament delivery devices is presented that has a plurality of interconnected stands, with each stand being configured to support a medicament delivery device and where the arrangement is configured such that each stand can be manually broken loose from an adjacent stand of the arrangement. A system is also presented where the arrangement contains a plurality of medicament delivery devices positioned in the arrangement.

17 Claims, 12 Drawing Sheets

(56) References Cited

U.S. PATENT DOCUMENTS

| | | | | |
|---|---|---|---|---|
| 2011/0108513 A1* | 5/2011 | Peter | ................ | B65D 21/0204 |
| | | | | 220/630 |
| 2015/0359708 A1* | 12/2015 | Boomgard | .............. | A61J 1/065 |
| | | | | 206/459.5 |
| 2018/0249848 A1* | 9/2018 | Goehring | ................ | A47F 5/005 |
| 2020/0155774 A1* | 5/2020 | Carpenter | ............... | F16B 47/00 |

FOREIGN PATENT DOCUMENTS

| | | | |
|---|---|---|---|
| IT | 2319727 | * | 4/1973 |
| WO | 2011/073916 A1 | | 6/2011 |
| WO | 2018/172099 A1 | | 9/2018 |

\* cited by examiner

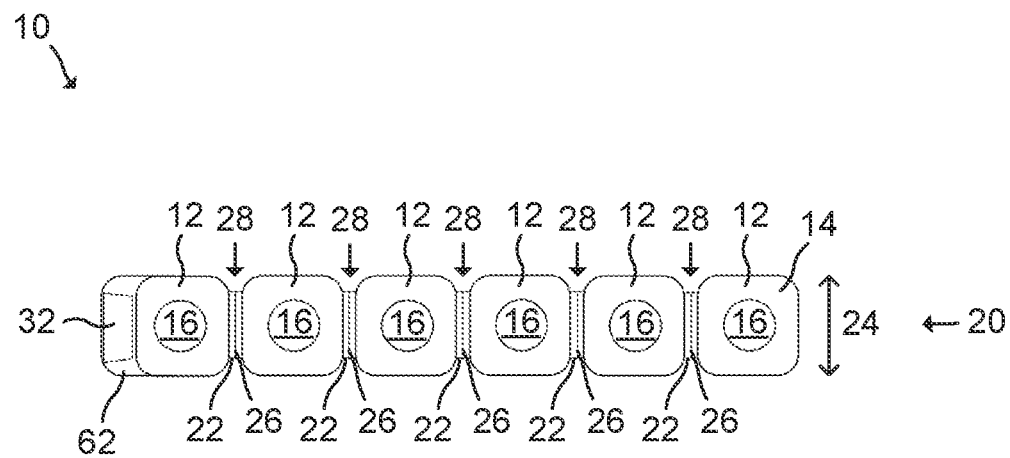
Fig. 12
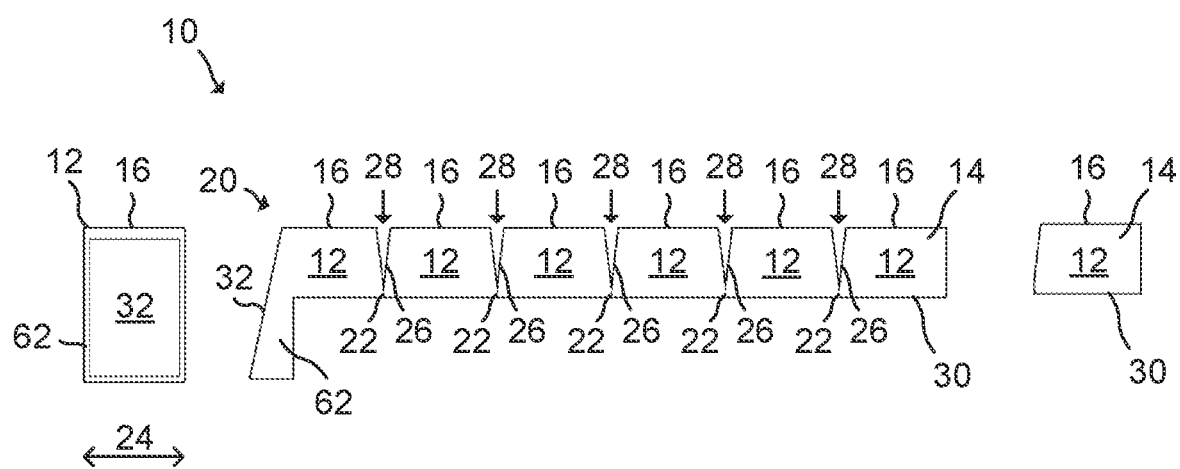
Fig. 13
Fig. 14

ARRANGEMENT FOR SUPPORTING MEDICAMENT DELIVERY DEVICES AND SYSTEM

CROSS REFERENCE TO RELATED APPLICATIONS

The present application is a U.S. National Phase Application pursuant to 35 U.S.C. § 371 of International Application No. PCT/EP2019/081915 filed Nov. 20, 2019, which claims priority to European Patent Application No. 18212151.7 filed Dec. 13, 2018. The entire disclosure contents of these applications are herewith incorporated by reference into the present application.

TECHNICAL FIELD

The present disclosure generally relates to an arrangement for supporting a plurality of medicament delivery devices. In particular, an arrangement for supporting a plurality of medicament delivery device, which arrangement comprises a plurality of interconnected stands, and a system comprising an arrangement and further comprising a plurality of medicament delivery devices, are provided.

BACKGROUND

Some types of medicaments can be stored for a long time and may be filled in containers, such as cartridges, syringes, ampoules, canisters or the like, containing a ready-to-use medicament in liquid state. However, some types of medicaments are a mixture of two substances, typically a dry medicament agent (such as lyophilized, powdered or concentrated liquid) and a diluent or solvent (such as water, dextrose solution or saline solution) in a liquid form. These types of medicaments cannot be pre-mixed and stored for a long time because the medicament agent is unstable and will lose its effect quickly due to degradation. Hence, a user has to perform the mixing within a limited time period prior to the delivery of a dose of medicament by manually operating a medicament delivery device. After the mixing, the dose may comprise both gas and medicament. In this case, the gas shall be removed prior to injection, otherwise when escaping it might expel the medicament and the dose of medicament may be smaller than intended.

In order to prevent the medicament degradation, a number of containers for medicaments requiring mixing have been developed comprising at least two chambers, known as multi-chamber containers. Multi-chamber containers typically comprise a first chamber containing the medicament agent in a dry or liquid form and at least one second chamber containing the liquid. These chambers may be sealed off by a stopper such that the medicament components are separated and do not become degraded. When the medicament components are to be mixed shortly before administering, a passage for the liquid is been opened between the chambers. The passage allows the mixing of the medicament agent and the liquid.

After mixing, the medicament delivery device with a medicament delivery member such as a e.g. needle, should typically be oriented substantially vertically in order to allow gases to escape for so called priming. After mixing and priming, typically from some seconds to several minutes, the mixed medicament is ready for delivery. Some users find it inconvenient to hold the medicament delivery device in the vertical orientation by hand during some time, in particular elder or disabled users. Therefore, a supporting device or a stand for keeping the medicament delivery device vertically is desired as a completing accessory.

SUMMARY

In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

One object of the present disclosure is to provide an arrangement for supporting a plurality of medicament delivery devices, which arrangement improves user experience.

A further object of the present disclosure is to provide an arrangement for supporting a plurality of medicament delivery devices, which arrangement provides an improved handling of the medicament delivery devices.

A still further object of the present disclosure is to provide an arrangement for supporting a plurality of medicament delivery devices, which arrangement provides an improved storage, such as a simpler and/or more compact storage, of the plurality of medicament delivery devices.

A still further object of the present disclosure is to provide an arrangement for supporting a plurality of medicament delivery devices, which arrangement has a simple and/or cheap design.

A still further object of the present disclosure is to provide an arrangement for supporting a plurality of medicament delivery devices, which arrangement solves several or all of the foregoing objects in combination.

A still further object of the present disclosure is to provide a system comprising an arrangement and a plurality of medicament delivery devices, which system solves one, several or all of the foregoing objects.

According to one aspect, there is provided an arrangement for supporting a plurality of medicament delivery devices, the arrangement comprising a plurality of interconnected stands, each stand being configured to support a medicament delivery device; wherein the arrangement is configured such that each stand can be manually broken loose from an adjacent stand of the arrangement.

Each stand may be configured to support an elongated medicament delivery device. To this end, each stand may comprise a holding structure for holding the medicament delivery device. The holding structure may for example be constituted by an opening for receiving and holding a distal end of the medicament delivery device. The opening may have one of a circular, oval and polygonal shape for holding the medicament delivery device. The stands may alternatively be referred to as support units or support caps.

The stands may be connected to each other in series to form a bar. The arrangement may for example comprise three to ten stands arranged in series, e.g. in a row. The bar may define a longitudinal direction.

Each stand may be configured to be manually broken loose by tilting the stand relative to an adjacent stand of the arrangement. In case the stands form a bar and the bar is positioned on a horizontal surface, each stand may be tilted relative to an adjacent stand of the arrangement about a horizontal axis substantially perpendicular to, or perpendicular to, the longitudinal axis of the bar. In other words, each stand may be tilted relative to an adjacent stand of the arrangement about an axis that is parallel with a width direction of the bar.

Each stand may be configured to be manually broken loose from an adjacent stand of the arrangement while supporting a medicament delivery device. In this way, a user may grab and tilt one of the medicament delivery devices in order to separate the stand holding the grabbed medicament delivery device from the arrangement.

Each stand may be configured to hold an elongated medicament delivery device in a substantially vertical orientation, or vertical orientation, when the stand is positioned on a substantially horizontal surface, or horizontal surface. This may apply to both interconnected stands and to separated stands.

When separated from the arrangement, the stand may be used to hold the medicament delivery device in a substantially vertical orientation during priming (e.g. after mixing of the liquid and the dry medicament component contained in a medicament delivery device). The vertical positioning (or substantially vertical positioning) of the medicament delivery device with the delivery member oriented upwards improves handling of the medicament delivery device since this orientation makes the medicament delivery device easy to grasp. For example, a user may easier remove a protective cap from the medicament delivery device while it being supported by the separate stand. The separated from the arrangement stand or the interconnected stands may further be used for stable storage of a medicament delivery device.

Furthermore, the vertical positioning (or substantially vertical positioning) of the medicament delivery device enables gas that appears during mixing of the medicament components to escape. Thus, each stand can ensure that a supported medicament delivery device is oriented in the proper position and thus primed before use.

According to one variant, each stand of the arrangement is a self-righting stand (not illustrated) that, when separated from the arrangement or interconnected state, is configured to move from an unbalanced position to an upright position. When the stand adapts the upright position, an elongated medicament delivery device is held by the stand in a substantially vertical, or vertical, orientation with the delivery member pointing upwards.

The plurality of separate stands may be connected by webs in an arrangement. The webs may for example be integrally formed with bodies of the stands, e.g. by injection molding the webs together with bodies, or as a part of bodies, of the stands. Each web may for example have a thickness of 0.5 to 5 mm.

Each web may be provided with a weakened structure to predefine a breaking region between two adjacent stands. The weakened structure may be a notch. Each notch may form a notch angle that is in the range of 40 degrees to 100 degrees. A notch may be provided on one or both sides of the connecting web.

Alternatively or additionally, the weakened structure of the may be a perforation. In any case, the weakened structure may extend over an entire width of the connecting web, e.g. perpendicular to a longitudinal direction of the bar.

The each stand in the arrangement or alternatively the entire arrangement may further comprise a reader component for reading information from an information carrier in a medicament delivery device supported by one of the stands. The reader may be provided in one or more of the stands. The information carrier may for example be an RFID tag encoded with information associated with the medicament delivery device and/or medicament.

The reader may be configured to read temperature information from information carriers in one or more of the medicament delivery devices. Each information carrier may for example be provided in an injector rigid needle shield (RNS) or in a flexible needle shield (FNC) of the medicament delivery device. The reader may for example be an NFC (Near-field communication) reader or an RFID (Radio-frequency identification) reader. The arrangement may comprise alternative types of suitable radio frequency reader component that can collect and transmit information.

A reading distance of the reader may for example be up to 40 mm. The reader may be constituted by a reader-writer, i.e. a device for both reading and writing information from/to the information carrier.

The arrangement may further comprise a screen configured to display information to a user. The information may be related to one or more of the medicament delivery devices supported by the stands. For example, temperature information, drug expiry information, medicament manufacture date, batch number, medicament type and/or medicament concentration may be displayed on the screen. Alternatively, or in addition, the arrangement may comprise a speaker for audibly communicating information related to one or more of the medicament delivery devices to a user.

The arrangement may further comprise a control unit, such as a microprocessor. The control unit may be provided in one or each of the stands in the bar. The stand comprising the control unit may be referred to as a control stand, mother stand or head stand. Also the screen may be provided on the control stand or all the stand in the bar.

The arrangement may further comprise a power source, such as a battery. The battery may be rechargeable. The power source may be configured to power the control unit and optionally further devices, such as the screen. Alternatively, or in addition, the arrangement may be powered by a mains power supply or alternative external power source.

The arrangement may further comprise a wireless communication module. The control unit may be configured to transmit, via the communication module, a signal comprising information read from one or more information carriers of the medicament delivery devices, e.g. to a mobile device or to a computer. The communication module may be configured to communicate via a wireless communication protocol, such as Bluetooth, GSM (Global System for Mobile communications) or Wi-Fi.

The reader component may comprise at least one antenna arranged to be broken when one of the stands is broken loose from an adjacent stand of the bar arrangement. One or more antennas may run through the several stands.

The reader may comprise a plurality of antennas, each antenna being associated with one of the stands. In this case, each antenna may be arranged to be broken when the associated stand is broken loose from an adjacent stand of the bar of the arrangement. For example, the arrangement may comprise a control unit provided in one of the stands. In this case, the plurality of antennas may run from the stand comprising the control unit to each of several or all of the other stands of the arrangement bar. The control unit may be configured to receive, via the antenna, a signal comprising information from the information carrier via a radio frequency protocol. The control unit may be configured to detect when one antenna is broken and may be configured to thereby conclude that the stand associated with this antenna has been broken loose. Each antenna may be a coil antenna comprising a coil and electric lines connected to the coil. In this case, the electric lines may be broken when breaking loose one of the stands from an adjacent stand of the arrangement.

The arrangement may further comprise a support device for slidingly supporting the plurality of the interconnected stands thereon. Due to the sliding support, the support device forms a delivery system. A user may for example place the bar of stands into or onto the support device. The user may then move the bar relative to the support device such that the outermost stand protrudes or extends from the support device. The user may then break loose the protruding/extending stand holding a medicament delivery device.

The support device may comprise the reader. Alternatively, or in addition, the support device may further comprise the screen configured to display information to the user, the control unit, the power source and/or the communication module.

According to a further aspect, there is provided a system comprising an arrangement according to the present disclosure. The system may further comprise a plurality of medicament delivery devices, for example a plurality of elongated medicament delivery devices such as injectors or inhalers. Each medicament delivery device may comprise an elongated tubular housing.

A medicament delivery device according to the present disclosure may comprise at least two chambers for containing agents to be manually mixed before being delivered. The medicament delivery device may for example be an injection device for injecting a medicament, such as a drug mixture, by a user.

Each medicament delivery device may comprise an information carrier. The information carrier may be used to log temperature information of medicament delivery device, for example through a supply chain and/or during storage. The information carrier may be an NFC chip or an RFID chip.

The system may further comprise a package for housing the arrangement and the plurality of medicament delivery devices supported by the stands of the arrangement. In case the arrangement comprises a screen, the package may comprise an opening aligned with the screen when the arrangement is enclosed into the package. Thereby, the screen can be seen from the exterior of the package without opening the package.

BRIEF DESCRIPTION OF THE DRAWINGS

Further details, advantages and aspects of the present disclosure will become apparent from the following embodiments taken in conjunction with the drawings, wherein:

FIG. 12 schematically represents a top view of an arrangement of a stand bar;

FIG. 13 schematically represents a front view of the arrangement in FIG. 12;

FIG. 14 schematically represents a side view of the arrangement in FIGS. 12 and 13 and a separated stand;

DETAILED DESCRIPTION

Figure 1:
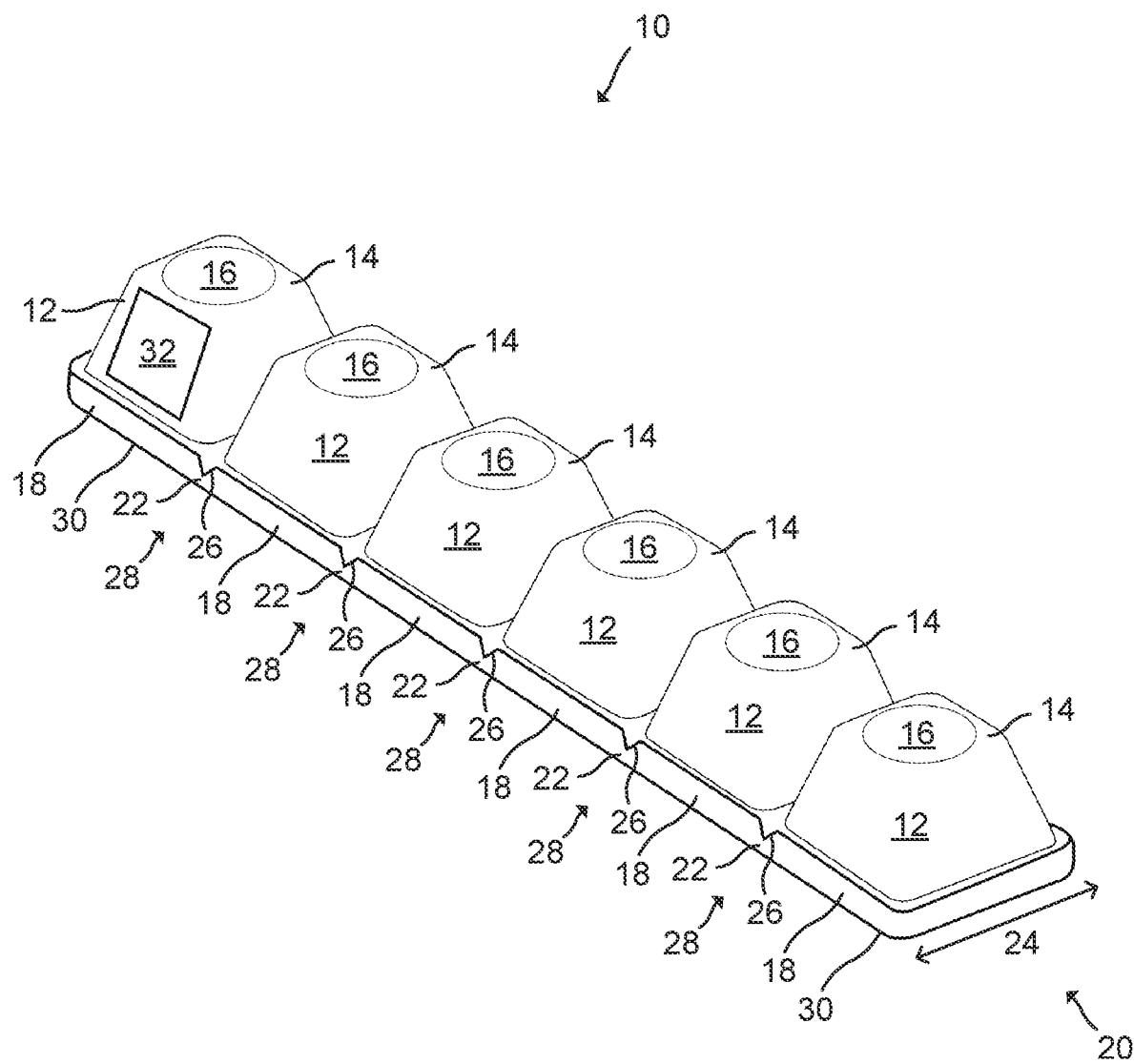
FIG. 1 schematically represents a perspective view of an arrangement or a bar of the stands.

In the following, an arrangement for supporting a plurality of medicament delivery devices comprises a plurality of interconnected stands, and a system comprising an arrangement and further comprising a plurality of medicament delivery devices, will be described. The same reference numerals will be used to denote the same or similar structural features.

FIG. 1 schematically represents a perspective view of an arrangement 10. The arrangement 10 comprises a plurality of interconnected stands 12. In this example, the arrangement 10 comprises six stands 12, but the number of stands 12 may differ. Each stand 12 comprises a body 14 and a holding structure 16 arranged in the body 14. Each body 14 comprises a base 18. The holding structure 16 is here constituted by a circular opening or receptacle in the body 14. Each stand 12 is configured to support one medicament delivery device (not shown) by means of the holding structure 16.

As shown in FIG. 1, the stands 12 are connected to each other in a row and thereby form a bar 20. The bar 20 defines a longitudinal axis (not denoted) of the arrangement 10. The stands 12 are connected to each other by means of intermediate connecting parts or webs 22. Each web 22 forms a bridge between two adjacent stands 12. In FIG. 1, the webs 22 are integrally injection molded with the bases 18 of the stands 12. Thus, the webs 22 are formed at the bottom of the arrangement 10. The webs 22 may however connect the other parts of the bodies 14, and/or in other ways than by integral injection molding with parts of the bodies 14.

In this example, each web 22 extends over the entire width 24 of the arrangement 10. Alternatively, the web 22 width 24 perpendicular to the longitudinal axis might be smaller than the corresponding dimension of the stand 12. Each web 22 may for example have a thickness of approximately 2 mm.

FIG. 1 further shows that each web 22 is provided with a weakened structure 26. In this example, the weakened structures 26 are constituted by notches extending over the entire width 24 of the webs 22 or its part and having an angle of approximately 90 degrees. Each weakened structure 26 thereby defines a breaking region 28 between two adjacent stands 12. Alternative configurations or types of weakened structures 26, such as perforations, are conceivable.

In this example, each body 14 has a generally upwardly tapering shape on a square or rectangular base 18. The base 18 of each stand 12 provides a horizontal downwards facing support surface 30. In this example, the horizontal support surfaces 30 are flush with lower surfaces of the webs 22.

The arrangement 10 further comprises a screen 32 for displaying information to a user. The screen 32 is positioned on the body 14 of one of the two outermost stands 12 (the leftmost stand 12 in FIG. 1). The screen 32 is configured to display various types of information. The stand 12 comprising the screen 32 is referred to as a control stand 12. Alternatively, each supporting stand 12 for keeping the medicament delivery device in upright position might be provided with an individual screen 32 (not shown).

Figure 2:
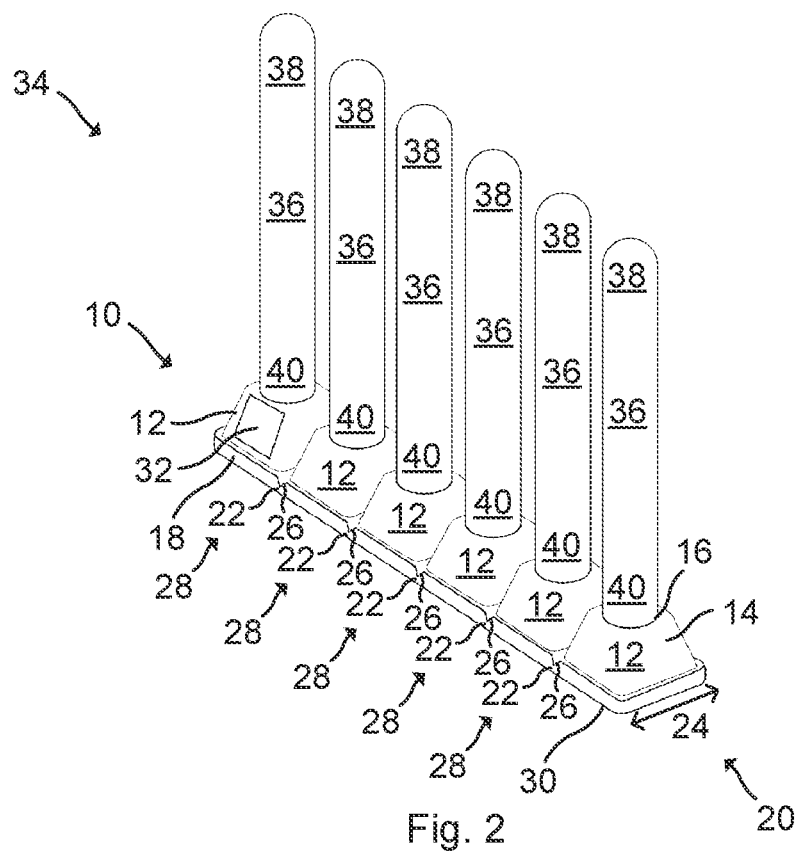
FIG. 2 schematically represents a perspective view of a system comprising the arrangement and a plurality of medicament delivery devices.
Figure 3:
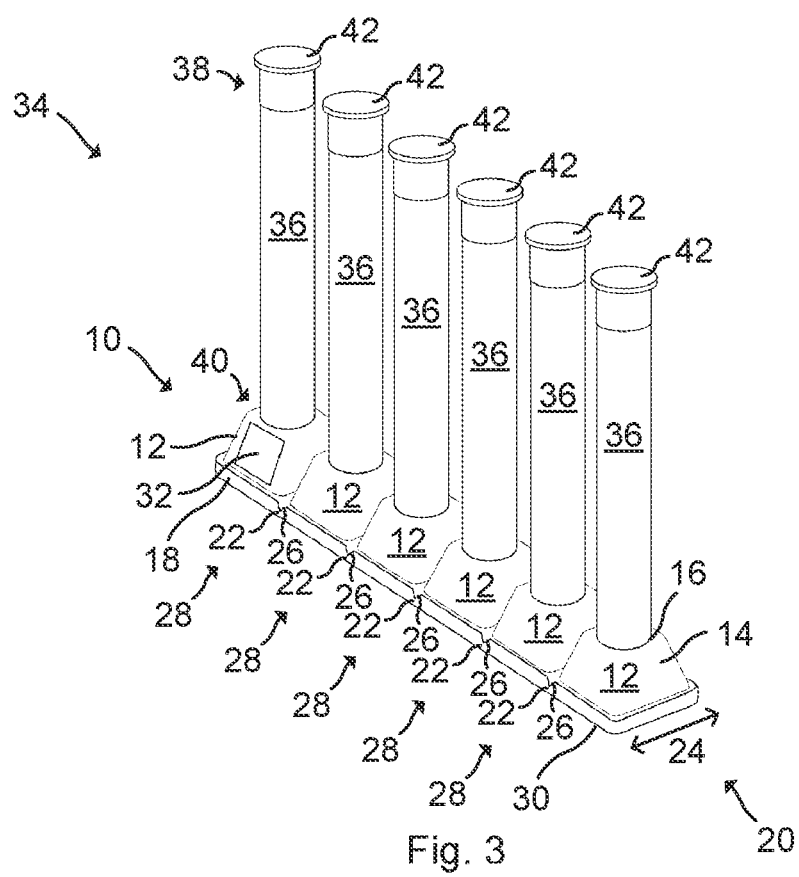
FIG. 3 schematically represents a perspective view of a system comprising the arrangement and a plurality of medicament delivery devices.

FIGS. 2 and 3 schematically represent a perspective view of a system 34 comprising the arrangement 10 and a plurality of elongated medicament delivery devices 36 inserted into the stands 12. In the example in FIG. 2, the medicament delivery devices 36 are injection devices. However, the system 34 may comprise alternative types of medicament delivery device 36 such as inhalers or the like.

The arrangement 10 supports the plurality of medicament delivery devices 36 on a horizontal surface (not illustrated). Each medicament delivery device 36 comprises a proximal end 38 for a delivery of the medicament and a distal end 40. Each stand 12 holds one medicament delivery device 36. More specifically, the holding structure 16 of each stand 12 holds the distal end 40 of the medicament delivery device 36. In this example, also the distal ends 40 of the medicament delivery devices 36 has a circular shape. The holding structure 16 of each stand 12 may be configured to firmly hold the distal end 40 of the medicament delivery device 36, for example by comprising an elastic material or due to a confirming shape of the holding structure 16.

As shown in FIG. 2, the arrangement 10 comprising the plurality of interconnected stands 12 as a bar 20 forms a compact storage for the medicament delivery devices 36. The system 34 may for example be stored in a refrigerator. The amount of the stands 12 with the medicament delivery devices 36 in each bar 20 allows to provide a daily, weekly or monthly amount of the medicament delivery devices in one package.

Figure 4:
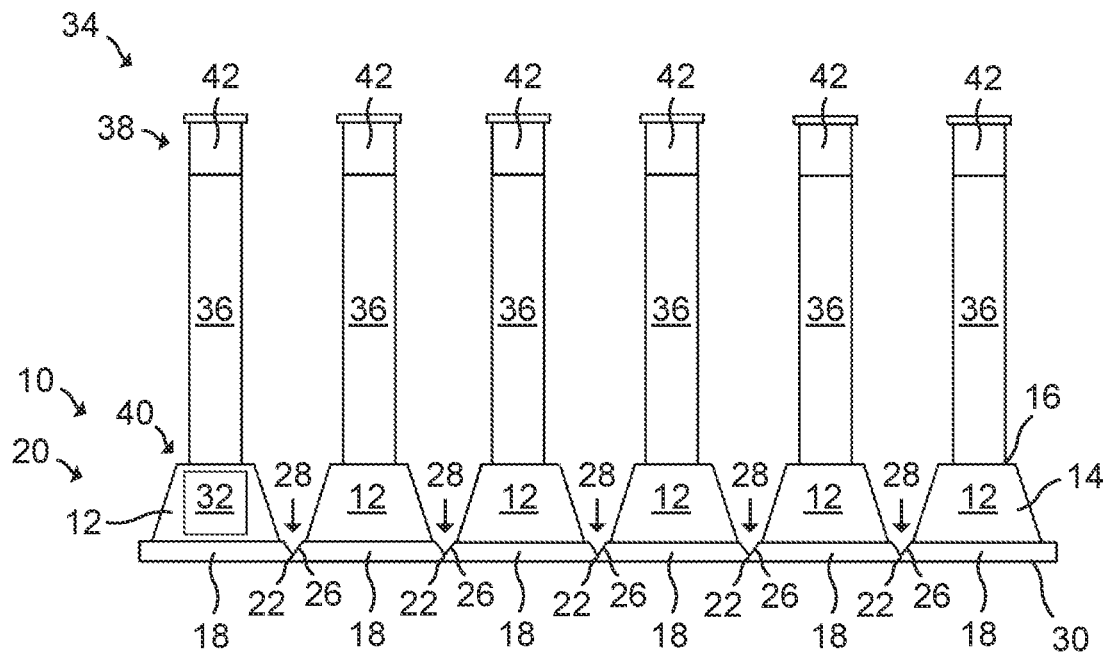
FIG. 4 schematically represents a side view of the system in FIG. 3.
Figure 5:
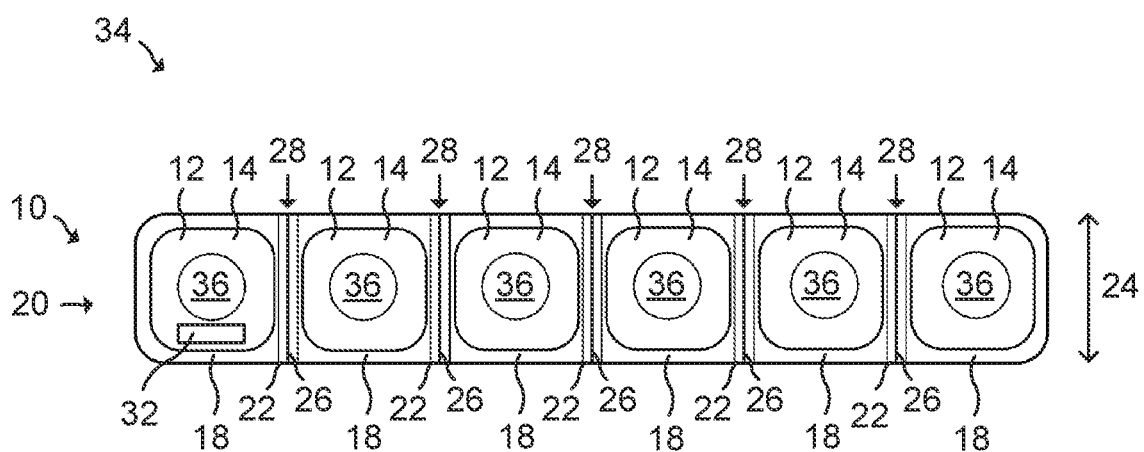
FIG. 5 schematically represents a top view of the system in FIGS. 3 and 4.

FIG. 3 schematically represents a perspective view of a system 34 comprising the arrangement 10 and a plurality of alternative elongated medicament delivery devices 36 provided with a protecting cap. FIG. 4 schematically represents a side view of the system 34 in FIG. 3, and FIG. 5 schematically represents a top view of the system 34 in FIGS. 3 and 4. The medicament delivery devices 36 in FIGS. 3 to 5 differ from FIG. 2 by each comprising an elongated tubular housing and the cap 42 attached to the housing at the proximal end 38 thereof. The arrangement 10 in FIGS. 1 to 5 is configured such that each stand 12 can be broken loose from an adjacent stand 12 of the arrangement 10 with manual force, e.g. by pulling, twisting and/or tilting at the weakened structure 26 of the web 22. As shown in FIGS. 2 to 5, each of the interconnected stands 12 of the arrangement 10 is configured to hold the elongated medicament delivery device 36 in a vertical orientation.

Figure 6:
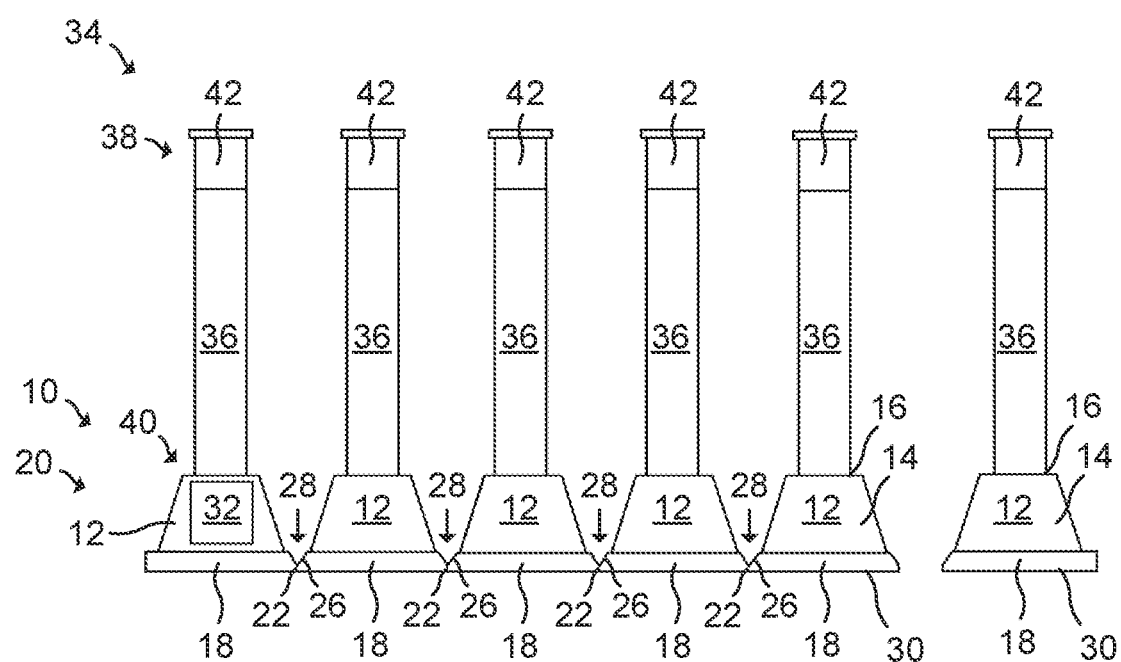
FIG. 6 schematically represents a side view of the system in FIGS. 3 to 5 when one stand with the medicament delivery device has been separated.

FIG. 6 schematically represents a side view of the system 34 in FIGS. 3 to 5 when the stand 12 has been broken loose from the remaining interconnected stands 12 of the arrangement 10. The rightmost stand 12 in FIG. 6 that has been broken loose is referred to as a separated individual stand 12. The arrangement 10 is configured such that each stand 12 of the arrangement 10 can be manually broken away from an adjacent stand 12. The leftmost control stand 12 is taken last.

The stand 12 can for example be separated from an adjacent stand 12 by manually grabbing an outermost medicament delivery device 36 and tilting this medicament delivery device 36 together with the associated stand 12 supporting the medicament delivery device 36, e.g. in the counterclockwise direction in FIG. 6. A counterclockwise tilting of a stand 12 in FIG. 6 is a rotating about a horizontal axis perpendicular to the longitudinal axis of the bar 20. During this tilting, the web 22 between the tilted stand 12 and the adjacent stand 12 will break in its breaking region 28, which breaking region 28 is in this example defined by the weakened structure 26 in the form of a notch. An outermost stand 12 may be separated from the arrangement 10 in alternative ways, for example by tilting in the opposite direction (clockwise in FIG. 6), by tilting about the longitudinal axis of the bar 20 and/or by pulling.

As shown in FIG. 6, the separated individual stand 12 is configured to hold the inserted in it medicament delivery device 36 in the vertical orientation when the separated stand 12 is positioned on a horizontal support surface. Prior to delivering a dose of medicament, a user may for example initiate mixing and remove the cap 42. The mixing may be initiated in various ways, for example by pushing a button, rotating two parts relative to each other or releasing a lock depending on the medicament delivery device design. When the mixing has been initiated, a first chamber containing a medicament agent and a second chamber containing a liquid are brought into communication. When the medicament agent and the liquid are mixed, air bubbles often develop. In order to release these bubbles or gases, the medicament delivery device 36 should be held in a substantially vertical orientation for some time by its proximal end pointing upwards, for example a few minutes. The separated stand 12 assists in priming by supporting the medicament delivery device 36 in a generally vertical orientation.

When the mixing has been initiated, the medicament delivery device 36 may be inserted into the separated stand 12. Alternatively, mixing of the medicament delivery device 36 may be initiated while already being supported by the separated stand 12. When the mixing has been initiated, the user may place the separated stand 12 with the inserted medicament delivery device 36 on a horizontal surface, such as on a kitchen countertop or on a table. The separated stand 12 holding the medicament delivery device 36 may also be carried during a travel. The arrangement 10 has a simple and cheap design, and provides a compact storage of the plurality of medicament delivery devices 36, and a simple separation of the stand 12 that can then be used to support the medicament delivery device 36 in a vertical orientation. Thus, the user experience and operation of the medicament delivery device is improved. The support surface 30 of each stand 12 may be provided with a friction increasing structure and/or a friction increasing material preventing a glide.

Figure 7:
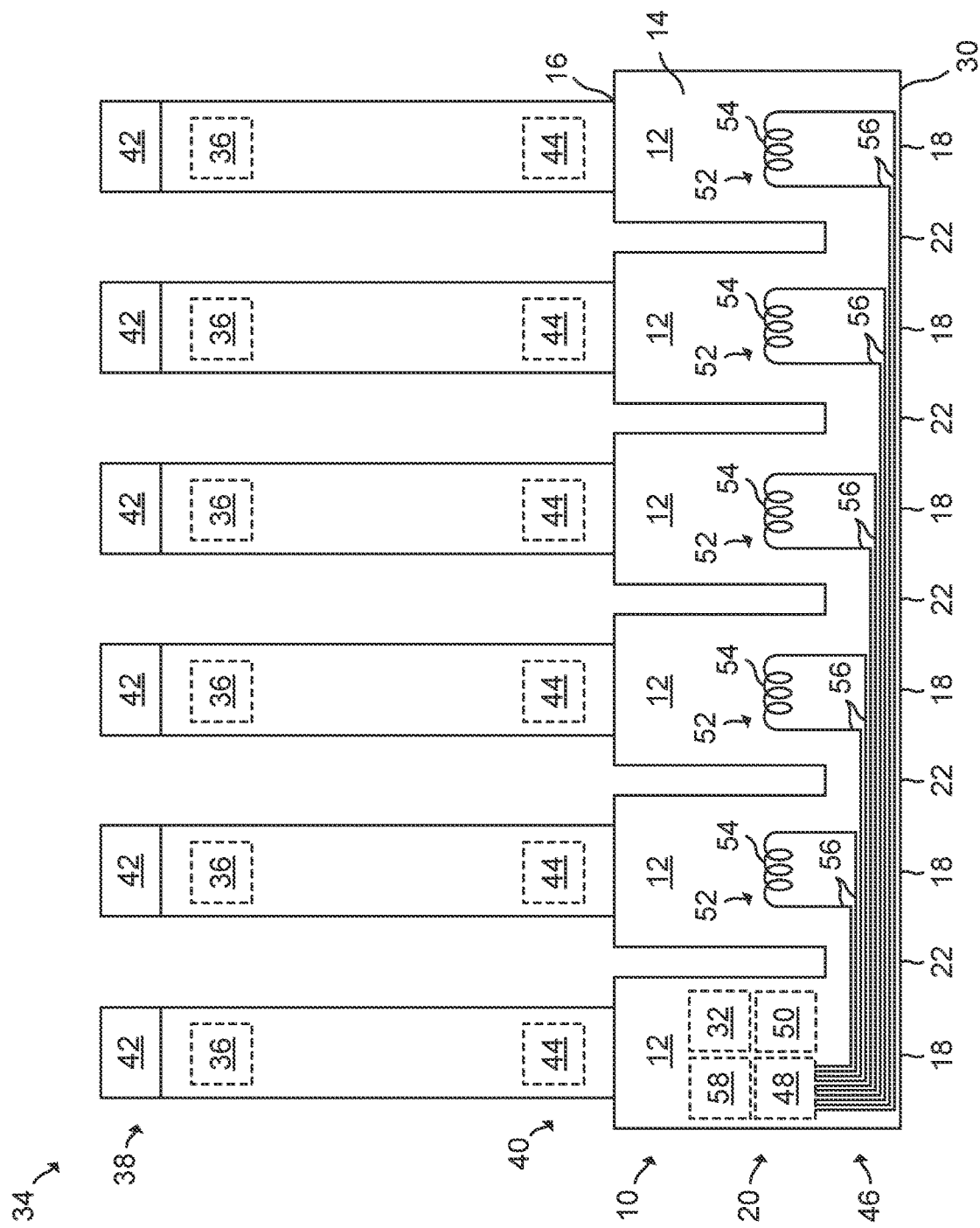
FIG. 7 schematically represents a side view of the system in FIGS. 3 to 6 illustrating a reader.

FIG. 7 schematically represents a side view of the system 34 in FIGS. 3 to 6. As shown in FIG. 7, each medicament delivery device 36 comprises an information carrier 44. In this example, the information carrier 44 is an RFID tag encoded with information associated with the medicament delivery device 36. Moreover, the information carrier 44 is provided in a distal end 40 of each medicament delivery device 36. The encoded information may for example be temperature information, drug expiry information, medicament manufacture date, batch number and medicament type and/or medicament concentration.

The arrangement 10 in FIG. 7 further comprises a reader 46. The reader 46 is configured to read the information from the information carriers 44 in the medicament delivery devices 36. The reader 46 may optionally also be configured to write information to the information carriers 44.

The arrangement 10 in FIG. 7 further comprises a control unit 48. In this example, the control unit 48 is provided in the control stand 12, i.e. the stand 12 comprising the screen 32. A power source 50, such as a rechargeable battery, is also provided in the control stand 12. The power source 50 is configured to power the control unit 48 and the screen 32.

In case the reader 46 is constituted by a reader-writer, the control unit 48 may for example control the reader 46 to write temperature information to the information carriers 44, e.g. temperatures to which the arrangement 10 has been exposed through a supply chain and/or during storage. To this end, the arrangement 10 may comprise a temperature sensor (not shown). Alternatively, temperature data may be wirelessly received from an external temperature sensor. The temperature information may be displayed on the screen 32.

In the example in FIG. 7, the reader 46 is an RFID reader. The reader 46 comprises a plurality of antennas 52. As shown in FIG. 7, each antenna 52 extends from the control stand 12 to each of the individual stand 12 of the arrangement 10. More specifically, each antenna 52 extends from the control unit 48 in the control stand 12, through at least one web 22 and to the each stand 12 associated with the antenna 52.

In the example in FIG. 7, each antenna 52 comprises a coil 54 and electric lines 56 connected to the coil 54 to form a closed circuit. By means of the antennas 52, the control unit 48 can detect how many medicament delivery devices 36 are presently supported by stands 12 in the arrangement 10.

Each antenna 52 is configured to power an information carrier 44 of a medicament delivery device 36 held by the stand 12 associated with the antenna 52. Upon receiving an electromagnetic signal from the antenna 52, the information carrier 44 in response sends information stored in its memory to the antenna 52. In this way, the control unit 48 can wirelessly obtain information, such as a status, from each of the medicament delivery devices 36 supported by the stands 12.

When the electric lines 56 through a web 22 are broken by separating the stand 12 from the arrangement 10, the control unit 48 can no longer read information from the information carrier 44, in the medicament delivery device 36 held by the separated stand 12, by means of the antenna 52. The control unit 48 can thereby also detect whether or not a circuit of antenna 52 is broken, i.e. whether the stand 12 associated with the antenna 52 has been broken loose from the arrangement 10. Each antenna 52 is thus arranged to be broken when one of the stands 12 is broken loose from an adjacent stand 12 of the arrangement 10.

The stand 12 of the example in FIG. 7 further comprises a wireless communication module 58. The communication module 58 may for example be a Wi-Fi device or a BLE (Bluetooth Low Energy) device. The communication module 58 may be used to wirelessly communicate with a smart phone or a computer, e.g. communicate the information read from the information carrier 44 of one or more of the medicament delivery devices 36.

Figure 8:
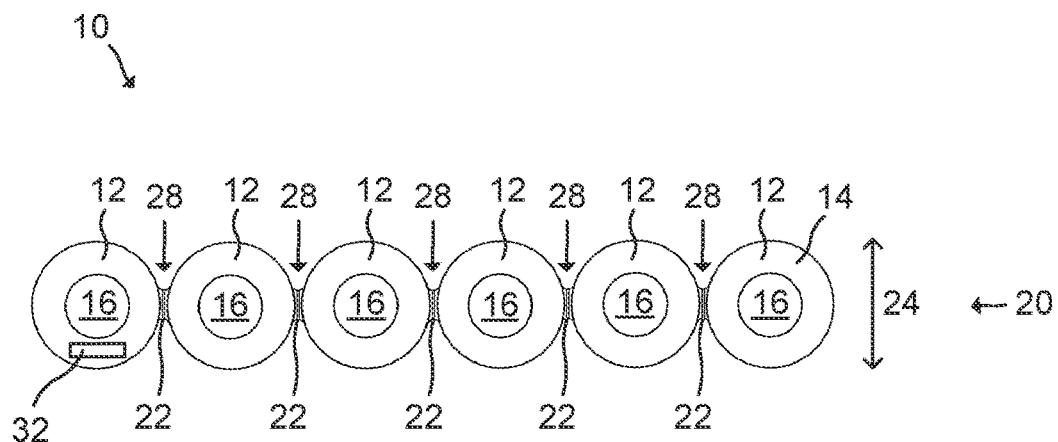
FIG. 8 schematically represents a top view of an arrangement of a bar of the self-righting stands with a circular circumferential shape of the stand.
Figure 9:
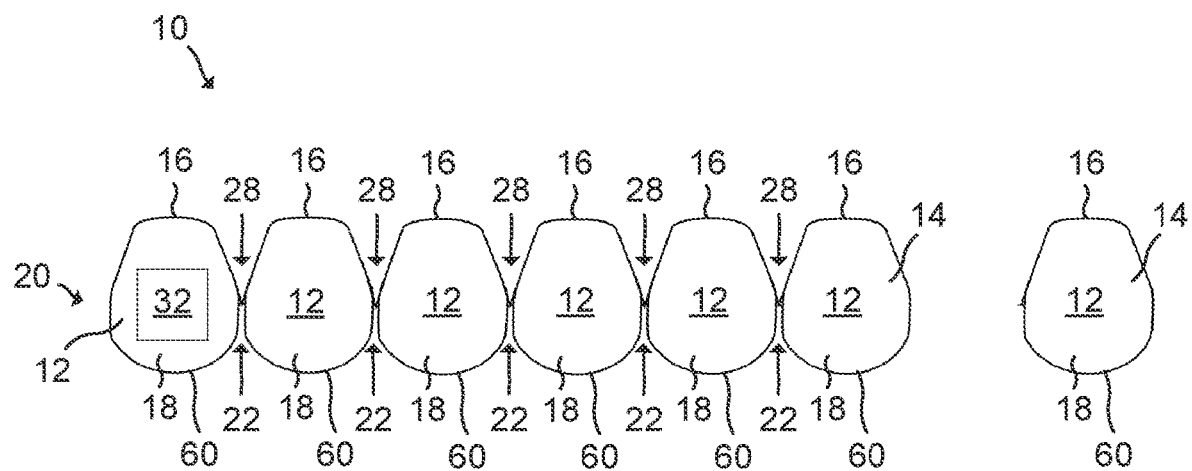
FIG. 9 schematically represents a side view of the arrangement in FIG. 8 and a separated individual self-righting stand.

FIG. 8 schematically represents a top view of an arrangement 10 and FIG. 9 schematically represents a side view of the arrangement 10 in FIG. 8 and a separated stand 12. With collective reference to FIGS. 8 and 9, mainly differences with respect to FIGS. 1 to 7 will be described. The arrangement 10 in FIGS. 8 and 9 comprises a plurality of interconnected self-righting stands 12. The webs 22 connecting the stands 12 do also not comprise any weakened structure 26, as in FIGS. 1 to 7. Rather, the webs 22 in FIGS. 8 and 9 are formed somewhat thinner than the webs 22 in FIGS. 1 to 7. The webs 22 in FIGS. 8 and 9 may for example have a thickness of approximately 0.5 mm.

When a separated stand 12 of such self-righting to a vertical position shape supporting the inserted medicament delivery device 36 is positioned on a substantially horizontal surface, the stand 12 is configured to swing and move from an unbalanced position to an upright vertical position. To this end, each stand 12 comprises a distally facing rounded support surface 60 and has a low center of gravity. The rounded support surface 60 has a continuous convex shape. Each stand 12 may for example comprise a weight positioned closed to its bottom or support surface 60. When the stand 12 is in the upright position, the medicament delivery device 36 held by the stand 12 may be oriented at an angle less than 30 degrees from a vertical direction.

The positioning of the center of gravity causes the stand 12 to rock from any unbalanced position, where the rounded support surface 60 is in contact with the substantially horizontal surface, to the upright position, which means that the holding structure 16 constituted by a circular opening or receptacle in the body 14 is facing upwards. The gravity force of the stand 12 generates a moment on the stand 12 and on the medicament delivery device 36 inserted into the holding structure 16 such that the stand 12 swings, and the medicament delivery device 36 held by the stand 12, are rotated from an unbalanced position, towards the upright vertical position of the medicament delivery device 36. The stand 12 and the medicament delivery device 36 will eventually become stable and at rest in the upright position. However, the rounded support surface 60 of the stand 12 causes the stand 12 to swing back and forth before becoming stable and at rest in the upright position. This movement of the stand 12 assists in mixing process due to swinging back and forth and priming by supporting the medicament delivery device 36 in a generally vertical orientation.

Figure 10:
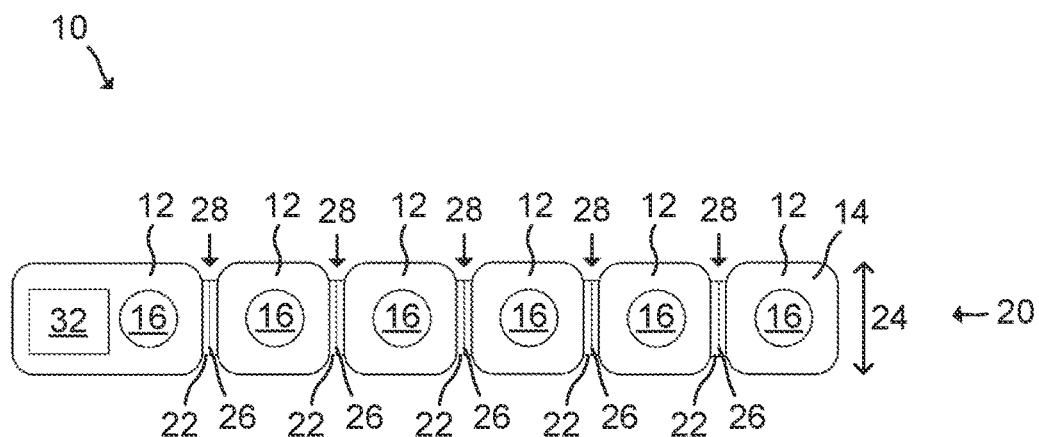
FIG. 10 schematically represents a top view of an arrangement of the stand bar with rectangular stands.
Figure 11:
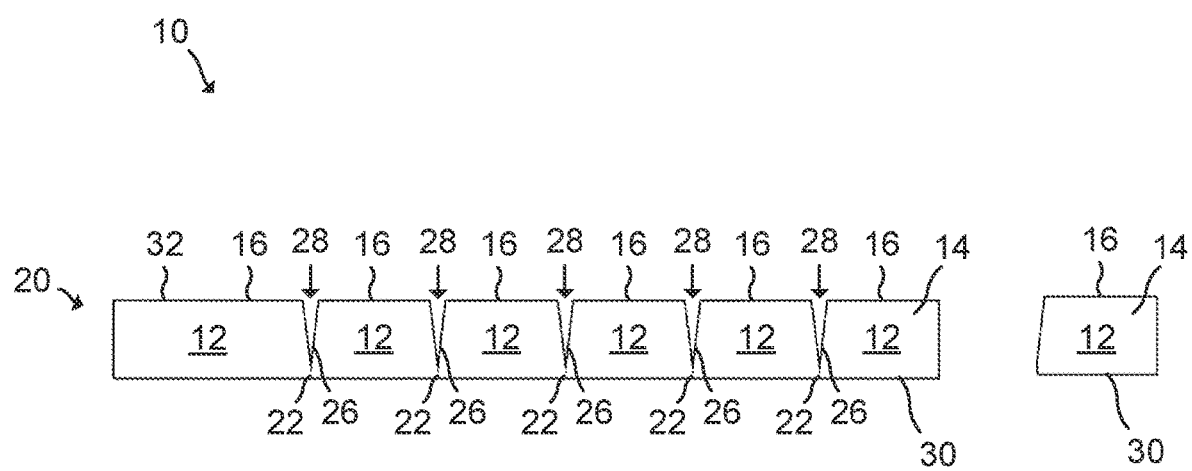
FIG. 11 schematically represents a side view of the arrangement of the stand bar in FIG. 10 and a separated individual stand.

FIG. 10 schematically represents a top view of an arrangement 10 and FIG. 10 schematically represents a side view of the arrangement 10 in FIG. 10 and the separated stand 12. Mainly differences with respect to FIGS. 1 to 9 will be described. In FIGS. 10 and 11, the control stand 12 comprising the screen 32 is horizontally elongated. The screen 32 is horizontally oriented on a horizontal top surface of the control stand 12.

FIG. 12 schematically represents a top view of an arrangement 10, FIG. 13 schematically represents a front view of the arrangement 10 in FIG. 12, and FIG. 14 schematically represents a side view of the arrangement 10 in FIGS. 12 and 13 and the separated stand 12. Mainly differences with respect to FIGS. 1 to 11 will be described. In FIGS. 12 to 14, the control stand 12 comprises a protruding portion 62. The protruding portion 62 may be integrally formed with the body 14 of the control stand 12. As shown in FIG. 14, the protruding portion 62 extends downwards below the horizontal support surface 30. The protruding portion 62 thereby forms a lip that for example improves alignment of the arrangement 10 on a shelf or a table edge. The protruding portion 62 also enables a larger display area on the screen 32. When using the arrangement 10 in FIGS. 12 to 14, the stand 12 opposite to the control stand 12 (the rightmost stand 12 in FIGS. 12 and 14), is broken loose first.

Figure 15:
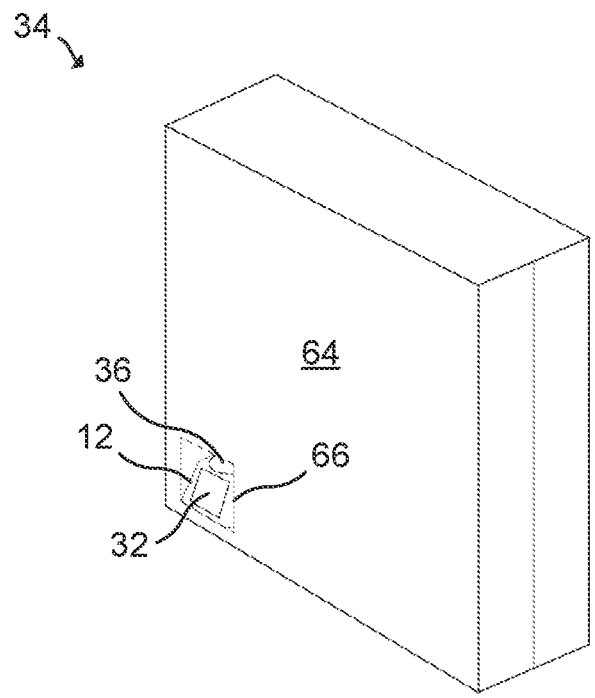
FIG. 15 schematically represents a perspective view of a system comprising a package and an arrangement visible though the opening in the package with a plurality of medicament delivery devices.
Figure 16:
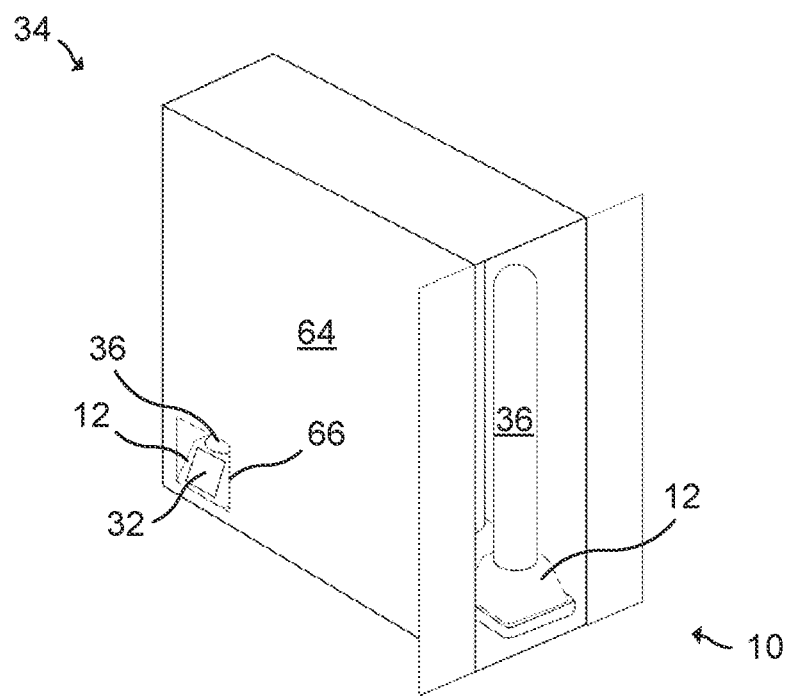
FIG. 16 schematically represents a perspective view of the system in FIG. 15 when the package is opened.

FIG. 15 schematically represents a perspective view of a system 34 comprising the arrangement 10, the plurality of medicament delivery devices 36 and a package 64. The package 64 comprises an opening 66. The medicament delivery devices 36 may be delivered together with the arrangement 10 in the package 64. When the system 34 is accommodated in the package 64, the screen 32 of the control stand 12 is aligned with the opening 66. In this example, the opening 66 is provided in a lower left corner of a front side of the package 64. A user receiving the package 64 can thereby read information from the screen 32 prior to opening the package 64. FIG. 16 schematically represents a perspective view of the system 34 in FIG. 16 when the package 64 is opened.

Figure 17:
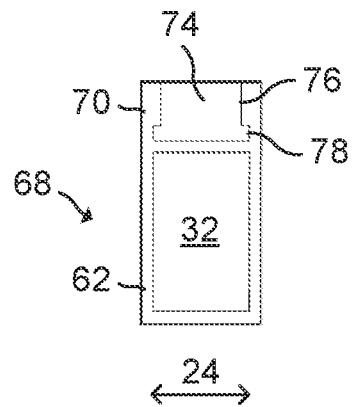
FIG. 17 schematically represents a front view of a support device for the stand bar.
Figure 18:
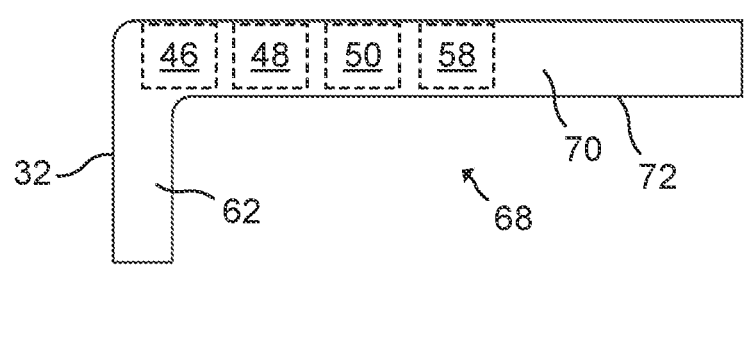
FIG. 18 schematically represents a side view of the support device in FIG. 17.
Figure 19:
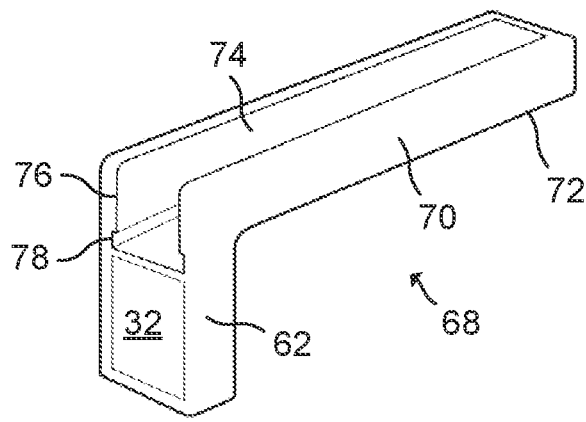
FIG. 19 schematically represents a perspective view of the support device in FIGS. 17 and 18.

FIG. 17 schematically represents a front view of a support device 68, FIG. 18 schematically represents a side view of the support device 68 in FIG. 17, and FIG. 19 schematically represents a perspective view of the support device 68 in FIGS. 17 and 18. With collective reference to FIGS. 17 to 19, mainly differences with respect to FIGS. 1 to 16 will be described.

The support device 68 in FIGS. 17 to 19 is configured to slidingly support the arrangement 10. The support device 68 comprises a base portion 70 and a protruding portion 62, similar to FIGS. 12 to 14, protruding downwardly from the base portion 70. The base portion 70 comprises a lower horizontal support surface 72. The support device 68 can thus be placed on a shelf or a table such that the protruding portion 62 hangs down from the edge of the shelf or table. The support device 68 may be fastened to the shelf/table by means of adhesive.

In the example in FIGS. 17 to 19, the base portion 70 of the support device 68 comprises a slot 74. The slot 74 comprises an upper narrow portion 76 and a lower wide portion 78. The slot 74 is formed horizontally along the base portion 70.

Furthermore, in the example in FIGS. 17 to 19, the support device 68 comprises the reader 46. The reader 46 is configured to read information from the information carrier 44 in the medicament delivery device 36, for example when passing by the reader 46. Also the reader 46 in the support device 68 may be an RFID reader for reading RFID information carriers 44. The support device 68 of this example also comprises the screen 32, the control unit 48, the power source 50 and the communication module 58. The screen 32 is provided in the protruding portion 62.

Figure 20:
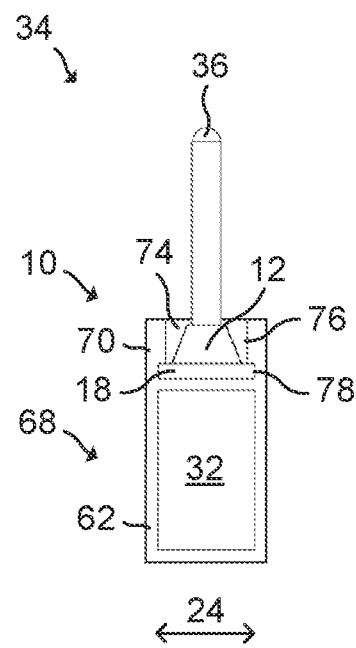
FIG. 20 schematically represents a front view of a system comprising an arrangement, a plurality of the medicament delivery devices and the support device in FIGS. 17 to 19.
Figure 21:
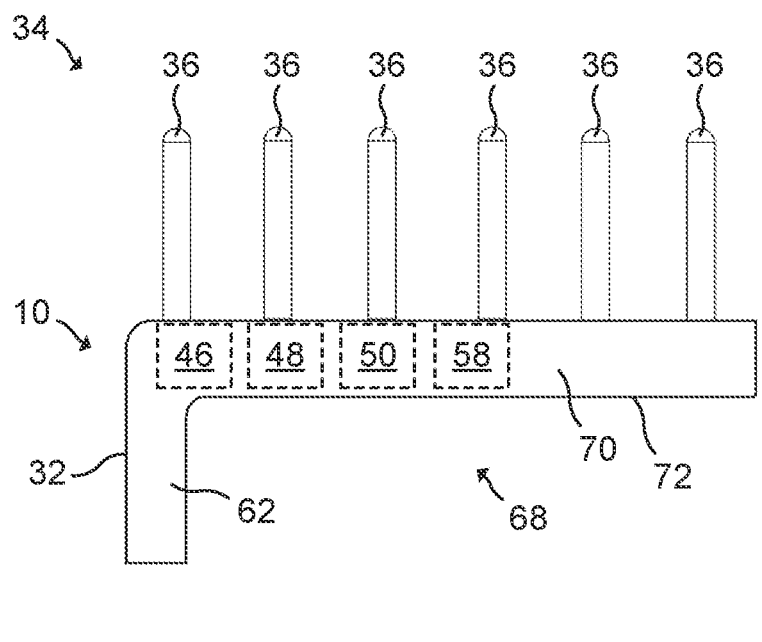
FIG. 21 schematically represents a side view of the system in FIG. 20.

FIG. 20 schematically represents a front view of a system 34 comprising the arrangement 10, the plurality of medicament delivery devices 36 and the support device 68 in FIGS. 17 to 19. FIG. 21 schematically represents a side view of the system 34 in FIG. 20, and FIG. 22 schematically represents a perspective view of the system 34 in FIGS. 20 and 21.

Figure 22:
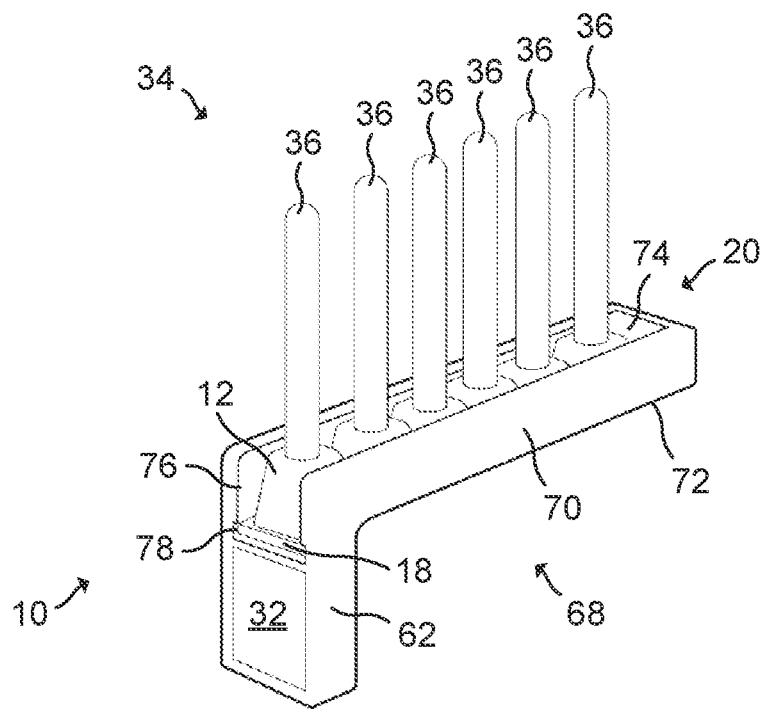
FIG. 22 schematically represents a perspective view of the system in FIGS. 20 and 21.

With collective reference to FIGS. 20 to 22, the support device 68 supports the arrangement 10 of the plurality of interconnected stands 12. Each stand 12 in turn supports the medicament delivery device 36. The arrangement 10 in FIGS. 20 to 22 is of the same shape as shown in FIGS. 1 to 7, but does not comprise any electronics. The arrangement 10 has been slid into the slot 74 of the support device 68. The width 24 of the bases 18 of the stands 12 corresponds to the width of the wide portion 78. The narrow portion 76 has a width smaller than the width 24 of the bases 18. According to one variant, the wide portion 78 may be wedge shaped, such as horizontally tapered away from the insertion opening, i.e. away from the screen 32. Thereby, it can be ensured that the arrangement 10 is slid into the support device 68 in a specific orientation, i.e. such that a particular stand 12 is taken out last. This may be the case if the support device 68 does not comprise any electronics, e.g. when supporting an arrangement 10 comprising a control stand 12 according to FIGS. 1 to 7. In this case, the control stand 12 may be positioned in or on the back of the support device 68 (to the right in FIG. 24).

Figures 23, 24:
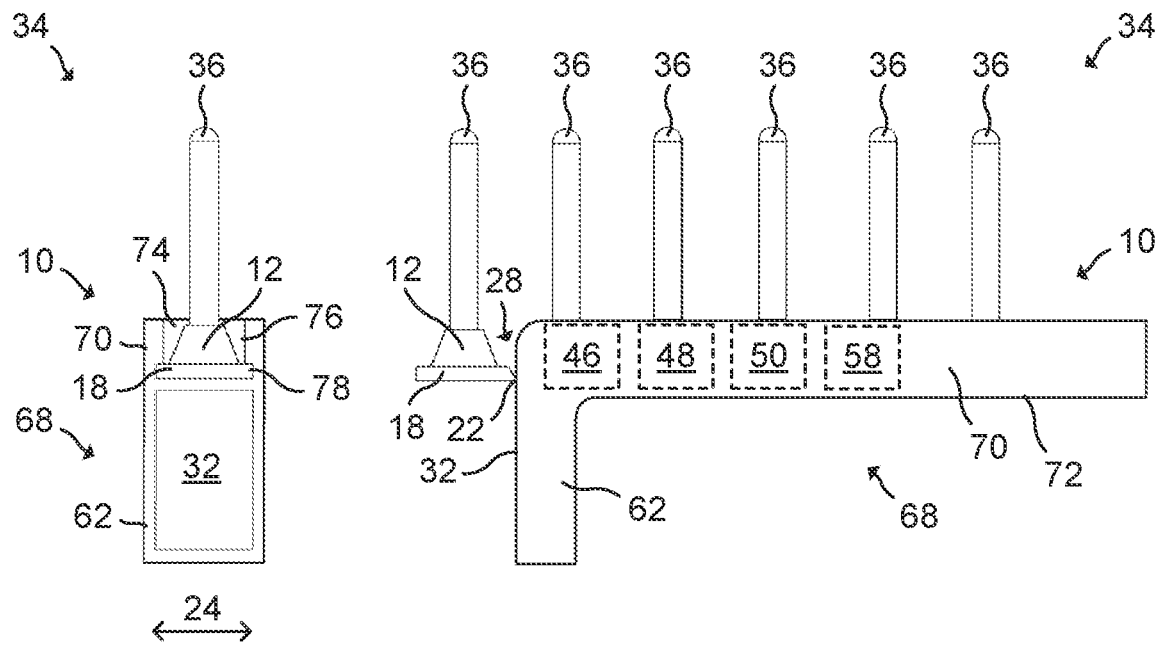
FIG. 23 schematically represents a front view of the system in FIGS. 20 to 22 when the arrangement has moved relative to the support device.
FIG. 24 schematically represents a side view of the system in FIG. 23.
Figure 25:
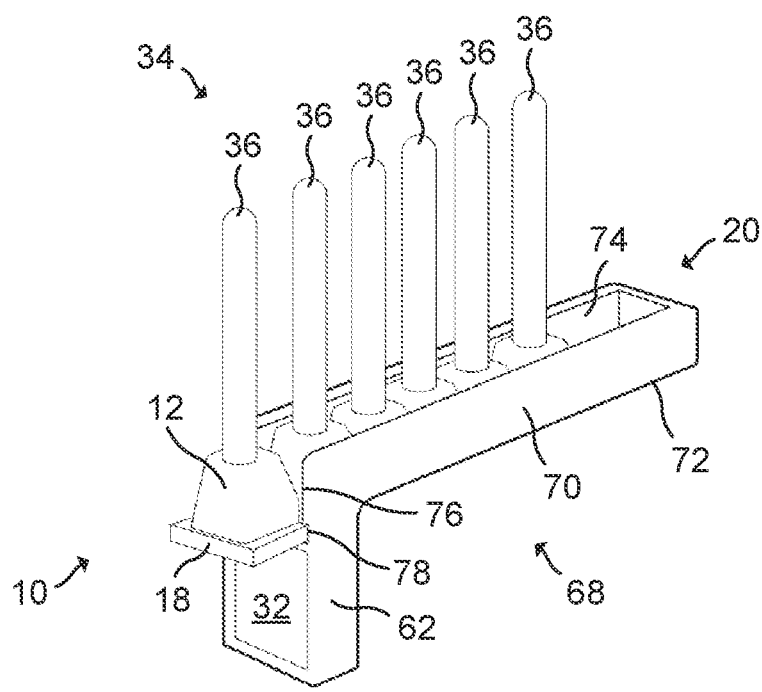
FIG. 25 schematically represents a perspective view of the system in FIGS. 23 and 24.

FIG. 23 schematically represents a front view of the system 34 in FIGS. 20 to 22 when the arrangement 10 has moved relative to the support device 68. FIG. 24 schematically represents a side view of the system 34 in FIG. 23, and FIG. 25 schematically represents a perspective view of the system 34 in FIGS. 23 and 24. With collective reference to FIGS. 23 to 25, a user may grab and pull the outermost medicament delivery device 36 (the leftmost in FIG. 24). During pulling, the bar 20 of stands 12 is linearly guided by means of the engagement of the bases 18 in the wide portions 78 of the slot 74 in the support device 68. When an outermost stand 12 holding the medicament delivery device 36 (the leftmost in FIG. 24) has been pulled out from the slot 74, the user may tilt the medicament delivery device 36 relative to the adjacent stand 12 of the arrangement 10. Thereby, the stand 12 is manually broken loose from an adjacent stand 12 of the arrangement 10. The support device 68 thus forms a delivery system for stands 12 supporting medicament delivery devices 36.

Since the remaining stands 12 of the arrangement 10 are engaged within the slot 74, due to the bases 18 held in the wide portion 78, the outermost stand 12 can be separated from the remaining stands 12 by one-hand operation. That is, the support device 68 provides a counter support.

By means of the reader 46, the control unit 48 reads information from the information carrier 44 in the medicament delivery device 36, e.g. from the medicament delivery device 36 that passes the reader 46. This information read may then be displayed on the screen 32.

When all the medicament delivery devices 36 have been consumed, a new arrangement 10 comprising stands 12 holding medicament delivery devices 36 can be inserted into the slot 74 of the support device 68. The support device 68 is thus reusable.

While the present disclosure has been described with reference to exemplary embodiments, it will be appreciated that the present disclosure is not limited to what has been described above. For example, it will be appreciated that the dimensions of the parts may be varied as needed.

The invention claimed is:

1. An arrangement for supporting a plurality of medicament delivery devices, each with a medicament delivery member, the arrangement comprising:

a plurality of interconnected stands, each stand being configured to support a medicament delivery device; and a support device for slidingly supporting the plurality of interconnected stands thereon, wherein the support device comprises a reader for reading information from an information carrier in a medicament delivery device supported by one of the stands, wherein each stand comprises a base and a receptacle configured with a circumference and a depth to accept and support a portion of an outer housing of the medicament delivery devices, wherein the base is wider than the circumference of the receptacle, wherein the arrangement is configured such that each stand can be manually broken loose from an adjacent stand of the arrangement, wherein, after being manually broken loose from the adjacent stand, each stand is configured to hold the elongated medicament delivery device in a vertical orientation when the stand is positioned on a horizontal surface with the medicament delivery member oriented upwards and perpendicular to the horizontal surface.

2. The arrangement according to claim 1, wherein the stands are connected to each other in series to form a bar.

3. The arrangement according to claim 1, wherein each stand is configured to be manually broken loose by tilting the stand relative to an adjacent stand of the arrangement.

4. The arrangement according to claim 1, wherein each stand is configured to be manually broken loose from an adjacent stand of the arrangement while supporting a medicament delivery device.

5. The arrangement according to claim 1, wherein the stands are connected by a web.

6. The arrangement according to claim 5, wherein each web is provided with a weakened structure to predefine a breaking region between two adjacent stands.

7. The arrangement according to claim 6, wherein the weakened structure is a notch having an angle of approximately 90 degrees.

8. The arrangement according to claim 1, further comprising a reader for reading information from an information carrier in a medicament delivery device supported by one of the stands.

9. The arrangement according to claim 8, wherein the reader comprises at least one antenna arranged to be broken when one of the stands is broken loose from an adjacent stand of the arrangement.

10. The arrangement according to claim 8, wherein the reader comprises a plurality of antennas, each antenna being associated with one of the stands, and wherein each antenna is arranged to be broken when the associated stands is broken loose from an adjacent stand of the arrangement.

11. A system comprising an arrangement according to claim 1 and further comprising a plurality of medicament delivery devices.

12. The system according to claim 11, wherein each medicament delivery device comprises an information carrier.

13. A collection of supporting units for holding a plurality of medicament delivery devices in an upright and vertical orientation, the collection comprising:

a plurality of interconnected stands, where each stand comprises a base and a receptacle configured with a circumference and a depth to accept and support a portion of an outer housing of the medicament delivery devices, and a reader for reading information from an information carrier operatively connected to each of the plurality of medicament delivery devices, wherein the reader comprises a support device for slidingly supporting the interconnected stands thereon, wherein the base is wider than the circumference of the receptacle, wherein each adjacent base comprises a web having a shared weakened structured defining a breaking region, and wherein the collection is configured such that each stand can be manually broken loose from an adjacent stand when the stands each contain one of the plurality of medicament delivery devices in an upright and vertical orientation, and wherein, after being manually broken loose from the adjacent stand, each stand is configured to support a given medicament delivery device of the plurality of medicament delivery devices in the upright and vertical orientation when the stand is positioned on a horizontal surface with the medicament delivery member oriented upwards and perpendicular to the horizontal surface.

14. The collection of claim 13, wherein the weakened structure is a notch having an angle of approximately 90 degrees.

15. The collection according to claim 13, wherein the reader comprises a plurality of antennas, where each of the plurality of antenna being associated with one of the stands.

16. The collection according to claim 15, wherein one of the plurality of antennas is arranged to be broken when one of the stands is broken loose from an adjacent stand in the plurality of interconnected stands.

17. The arrangement according to claim 1, further comprising:

a screen positioned on the base of one of the plurality of interconnected stands, wherein the screen is configured to display information relating to the plurality of medicament delivery devices.

* * * * *